US009278090B2

(12) United States Patent
Gutkind et al.

(10) Patent No.: US 9,278,090 B2
(45) Date of Patent: Mar. 8, 2016

(54) METHODS OF PREVENTING THE DEVELOPMENT OF MUCOSITIS AND RELATED DISORDERS

(71) Applicant: The United States of America, as represented by the Secretary, Department of Health and Human Services, Washington, DC (US)

(72) Inventors: J. Silvio Gutkind, Potomac, MD (US); Ramiro Iglesias-Bartolome, Bethesda, MD (US); Vyomesh Patel, Washington, DC (US); Ana p. Cotrim, Bethesda, MD (US); Alfredo Molinolo, Rockville, MD (US); James B. Mitchell, Damascus, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 24 days.

(21) Appl. No.: 13/798,863

(22) Filed: Mar. 13, 2013

(65) Prior Publication Data

US 2014/0066472 A1 Mar. 6, 2014

Related U.S. Application Data

(60) Provisional application No. 61/696,861, filed on Sep. 5, 2012.

(51) Int. Cl.
*A61K 31/436* (2006.01)

(52) U.S. Cl.
CPC ..................................... *A61K 31/436* (2013.01)

(58) Field of Classification Search
CPC .................................................. A61K 31/436
See application file for complete search history.

(56) References Cited

U.S. PATENT DOCUMENTS

| | | | |
|---|---|---|---|
| 3,929,992 | A | 12/1975 | Sehgal et al. |
| 2004/0258662 | A1* | 12/2004 | Gibbons et al. ............... 424/85.7 |
| 2009/0311249 | A1* | 12/2009 | Gianni et al. ............... 424/133.1 |
| 2010/0266590 | A1* | 10/2010 | Demetri et al. ............ 424/134.1 |
| 2011/0158983 | A1 | 6/2011 | Bascomb et al. |
| 2011/0252525 | P1 | 10/2011 | Dupont, Sr. |
| 2012/0276169 | A1* | 11/2012 | Kang et al. .................... 424/400 |

FOREIGN PATENT DOCUMENTS

| | | | |
|---|---|---|---|
| WO | WO 2004/004644 | A2 | 1/2004 |
| WO | WO 2008/027013 | A2 | 3/2008 |
| WO | WO 2010/022243 | A1 | 2/2010 |
| WO | WO 2011/014809 | A1 | 2/2011 |

OTHER PUBLICATIONS

Atkins et al. J. Clin. Oncol., 2004, vol. 22, No. 5, pp. 909-918.*
Reardon et al. Clin. Cancer Res., 2006, vol. 12, No. 3, part 1, pp. 860-868.*
Sarkaria et al. Int. J. Radiat. Oncol. Biol. Phys., Oct. 1, 2011, vol. 81, No. 2, pp. 468-475.*
Manegold et al. Clinical Cancer Research, 2008, vol. 14, pp. 898-900.*
Ekshyyan et al. Mol. Cancer Ther., 2009, vol. 8, pp. 2255-2265.*
Rodriguez-Caballero et al. Int. J. Oral Maxillofac. Surg., Feb. 2012, vol. 41, pp. 225-238.*
Amornphimoltham et al., "Mammalian target of rapamycin, a molecular target in squamous cell carcinomas of the head and neck," *Cancer Res.*, 65 (21), 9953-9961 (2005).
Amornphimoltham et al., "A retroinhibition approach reveals a tumor cell-autonomous response to rapamycin in head and neck cancer," *Cancer Res.*, 68 (4), 1144-1153 (2008).
Begg et al., "Strategies to improve radiotherapy with targeted drugs," *Nat. Rev. Cancer*, 11 (4), 239-253 (2011).
Blanpain et al., "Epidermal homeostasis: a balancing act of stem cells in the skin," *Nat. Rev. Mol. Cell Biol.*, 10 (3), 207-217 (2009).
Citrin et al., "Radioprotectors and mitigators of radiation-induced normal tissue injury," *Oncologist*, 15 (4), 360-371 (2010).
Czerninski et al., "Targeting mammalian target of rapamycin by rapamycin prevents tumor progression in an oral-specific chemical carcinogenesis model," *Cancer Prev. Res.*, 2 (1), 27-36 (2009).
Czerninski et al., "Optimizing the 4NQ0 oral carcinogenesis model for rapamycin chemoprevention," *Oral Oncology Supplement*, 3 (1) Supp. P2.89, 189-190 (2009).
Debacq-Chainiaux et al., "Protocols to detect senescence-associated beta-galactosidase (SA-βgal) activity, a biomarker of senescent cells in culture and in vivo," *Nat. Protoc.*, 4 (12), 1798-1806 (2009).
Feldman et al., "Active-Site Inhibitors of mTOR Target Rapamycin-Resistant Outputs of mTORC1 and mTORC2," *PLoS Biology*, 7 (2), 0371-0383 (2009).
Franken et al., "Clonogenic assay of cells in vitro," *Nat. Protoc.*, 1 (5), 2315-2319 (2006).
Hebert et al., "Hypoxia-inducible factor-1α polymorphisms and TSC1/2 mutations are complementary in head and neck cancers," *Mol. Cancer.*, 5 (3), 1-11 (2006).
Hou et al., "An activated mTOR/p70S6K signaling pathway in esophageal squamous cell carcinoma cell lines and inhibition of the pathway by rapamycin and siRNA against mTOR," *Cancer Lett.*, 253 (2), 236-248 (2007).
Iglesias-Bartolome et al., "mTOR inhibition prevents epithelial stem cell senescence and protects from radiation-induced mucositis," *Cell Stem Cell.*, 11 (3), 401-414 (2012).
Iglesias-Bartolome et al., "mTOR inhibition prevents epithelial stem cell senescence and protects from radiation-induced mucositis," Abstract from NIH CRM/SCIG Stem Cell Research Symposium, May 10-11, 2012.

(Continued)

*Primary Examiner* — James D Anderson
(74) *Attorney, Agent, or Firm* — Leydig, Voit & Mayer Ltd.

(57) ABSTRACT

Disclosed is a method of preventing the development of mucositis in a subject undergoing radiation therapy or chemotherapy for a disease in need thereof comprising administering an effective amount of a mammalian target of rapamycin (mTOR) inhibitor, such as rapamycin, to the subject. Further disclosed is a method of increasing the lifespan of a normal oral keratinocyte and/or reducing oxidative stress in a normal epithelial cell, wherein the method comprises administering an effective amount of an mTOR inhibitor to a subject undergoing radiation therapy or chemotherapy for a disease in need thereof.

21 Claims, 10 Drawing Sheets

(56) References Cited

OTHER PUBLICATIONS

Figure 1A:
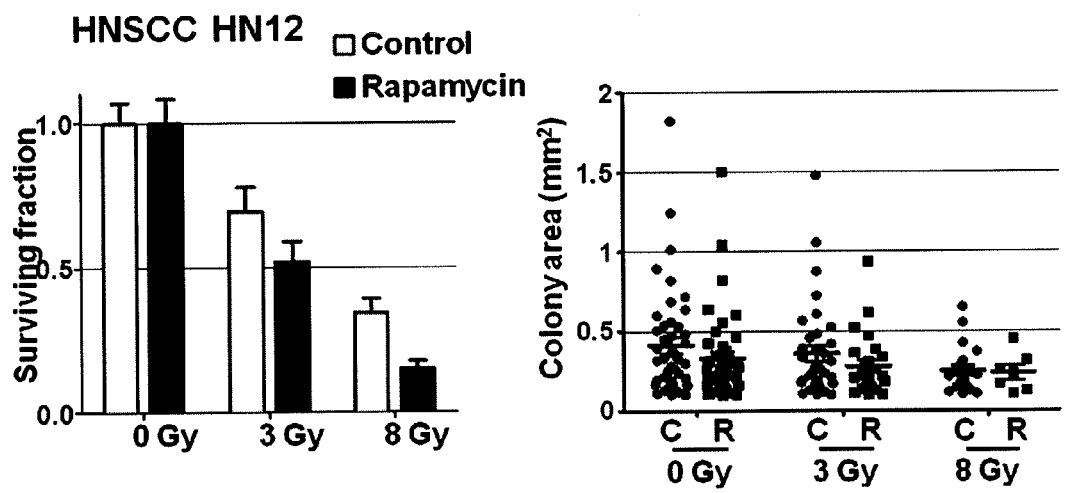

Iglesias-Bartolome et al., "mTOR inhibition prevents epithelial stem cell senescence and protects from radiation-induced mucositis," Poster from NIH CRM/SCIG Stem Cell Research Symposium, May 10-11, 2012.

International Preliminary Report on Patentability, Application No. PCT/US2009/054478, dated Feb. 22, 2011.

International Search Report, Application No. PCT/US2009/054478, dated Nov. 30, 2009.

Jimeno et al., "Dual EGFR and mTOR targeting in squamous cell carcinoma models, and development of early markers of efficacy," Br. J. Cancer, 96, 952-959 (2007).

Kuilman et al., "The essence of senescence," Genes Dev., 24 (22), 2463-2479 (2010).

Le Tourneau et al., "Molecular-targeted therapies in the treatment of squamous cell carcinomas of the head and neck," Curr. Opin. Oncol., 20 (3), 256-263 (2008).

Liu et al., "Expression and activity of mTOR and its substrates in different cell cycle phases and in oral squamous cell carcinomas of different malignant grade," Cell Biochem. Funct., 25 (1), 45-53 (2007).

Luis et al., "Regulation of human epidermal stem cell proliferation and senescence requires polycomb- dependent and -independent functions of Cbx4," Cell Stem Cell, 9 (3), 233-246 (2011).

Martin et al., "An NF-κB gene expression signature contributes to Kaposi's sarcoma virus vGPCR-induced direct and paracrine neoplasia," Oncogene, 27 (13), 1844-1862 (2008).

Nathan et al., "Mammalian target of rapamycin inhibitors as possible adjuvant therapy for microscopic residual disease in head and neck squamous cell cancer," Cancer Res., 67 (5), 2160-2168 (2007).

Nathan et al., "Overexpressed eIF4E is functionally active in surgical margins of head and neck cancer patients via activation of the Akt/mammalian target of rapamycin pathway," Clin. Cancer Res., 10 (17), 5820-5827 (2004).

Nonzee et al., "Evaluating the supportive care costs of severe radiochemotherapy-induced mucositis and pharyngitis : results from a Northwestern University Costs of Cancer Program pilot study with head and neck and non small cell lung cancer patients who received care at a county hospital, a Veterans Administration hospital, or a comprehensive cancer care center," Cancer, 113 (6), 1446-1452 (2008).

Oh et al., "Insulin-like growth factor-I receptor signaling pathway induces resistance to the apoptotic activities of SCH66336 (lonafarnib) through Akt/mammalian target of rapamycin-mediated increases in survivin expression," Clin. Cancer Res., 14 (5), 1581-1589 (2008).

Raimondi et al., "Rapamycin Prevents Early Onset of Tumorigensis in an Oral-Specific K-ras and p53 Two-Hit Carcinogenesis Model," Cancer Res., 69 (10), 4159-4166 (2009).

Richards, David J., "Synthesis and Anti-Tumor Properties of Pyrazolopyrimidines: Potent, ATP Competitive, and Selective Inhibitors of the Mammalian Target of Rapamycin (mTOR)," in Schulte, II, et al.'s Trip Report for "Chemistry in Cancer Research: A Vital Partnership in Cancer Drug Discovery and Development," New Orleans, LA, Feb. 8-11, 2009.

Rodier et al., "Four faces of cellular senescence," J. Cell. Biol., 192 (4), 547-556 (2011).

Sonis, "Mucositis: The impact, biology and therapeutic opportunities of oral mucositis," Oral Oncol., 45 (12), 1015-1020 (2009).

Sonis, "New thoughts on the initiation of mucositis," Oral Dis., 16 (7), 597-600 (2010).

Squarize et al., "Chemoprevention and treatment of experimental Cowden's disease by mTOR inhibition with rapamycin," Cancer Res., 68 (17), 1-7 (2009).

Vitolo et al., "The stable nitroxide tempol facilitates salivary gland protection during head and neck irradiation in a mouse model," Clin. Cancer Res., 10 (5), 1807-1812 (2004).

Yoshioka et al., "The Activation of AKT During Preoperative Chemotherapy for Esophageal Cancer Correlates With Poor Prognosis," Oncol. Rep., 19 (5), 1099-1107 (2008).

Zeng, "Human embryonic stem cells: mechanisms to escape replicative senescence?," Stem Cell Rev., 3 (4), 270-279 (2007).

\* cited by examiner

FIGURE 4A
FIGURE 4B
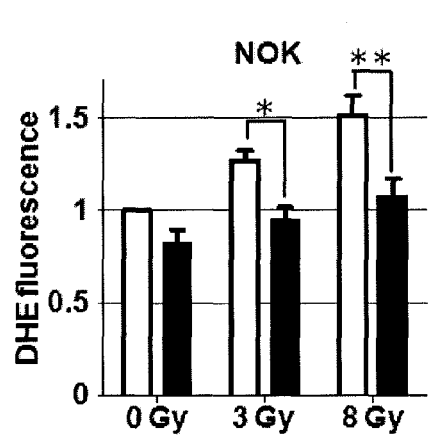
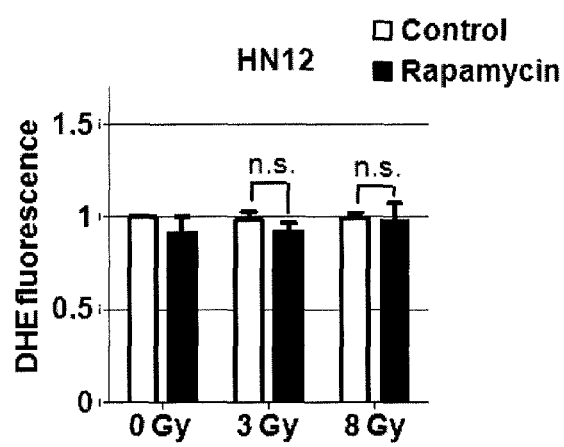
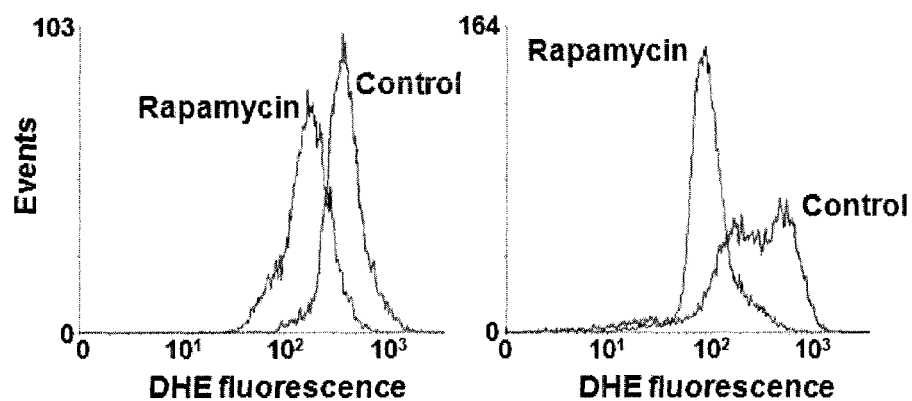
FIGURE 4C
FIGURE 4D

METHODS OF PREVENTING THE DEVELOPMENT OF MUCOSITIS AND RELATED DISORDERS

CROSS-REFERENCE TO A RELATED APPLICATION

This patent application claims the benefit of U.S. Provisional Patent Application No. 61/696,861, filed Sep. 5, 2012, which is incorporated herein by reference in its entirety.

BACKGROUND OF THE INVENTION

Both epidermis and mucosal epithelia are highly dependent on resident self-renewing stem cells, making them particularly vulnerable to physical and chemical insults compromising the repopulating capacity of the epithelial stem cell compartment. This is often the case in cancer patients receiving radiation or chemotherapy, many of whom develop mucositis, a debilitating condition involving painful and deep mucosal ulcerations as a result of damage to the normal tissue (Sonis, *Oral Oncol.*, 45, 1015-1020 (2009); Sonis, *Oral Diseases*, 16, 597-600 (2010)). Mucositis causes distress to the patients and results also in substantial increase in per-patient care cost (Nonzee et al., *Cancer* 113, 1446-1452 (2008)). Radiotherapy is one of the most widely used cancer treatments (Begg et al., *Nat. Rev. Cancer*, 11, 239-253 (2011)), and although technical advances now allow a more targeted delivery of radiation to the cancer cells, indirect damage to the normal surrounding tissues still remains a common and frequently weakening side effect (Citrin et al., *The Oncologist*, 15, 360-371 (2010)). Hence, therapeutic interventions that can reduce the deleterious effects of chemotherapy or radiation on normal epithelial stem cells are needed that will improve on the quality of life of cancer patients and treatment outcome.

BRIEF SUMMARY OF THE INVENTION

The present invention provides a method of preventing the development of mucositis in a subject undergoing radiation therapy or chemotherapy for a disease in need thereof comprising, consisting essentially of, or consisting of administering an effective amount of a mammalian target of rapamycin (mTOR) inhibitor to the subject.

It has been surprisingly found that mTOR inhibition protects normal epithelial progenitor cells (e.g., hair follicles and oral epithelial cells) from ionizing radiation-induced epithelial stem cell depletion. In addition, it has been found that inhibition of mTOR increases the clonogenic capacity of primary human oral keratinocytes and their resident self-renewing cells by preventing stem cell senescence. Accordingly, the present invention provides a method of increasing the lifespan of a normal oral keratinocyte in a subject undergoing radiation therapy or chemotherapy for a disease in need thereof comprising, consisting essentially of, or consisting of administering an effective amount of an mTOR inhibitor to the subject. Also provided is a method of preventing (including minimizing or reducing) hair loss in a subject undergoing radiation therapy or chemotherapy for a disease in need thereof comprising, consisting essentially of, or consisting of administering an effective amount of an mTOR inhibitor to the subject.

The invention further provides a method of reducing oxidative stress in a normal epithelial cell compared to a cancerous epithelial cell (e.g., from an oral mucosa) in a subject undergoing radiation therapy or chemotherapy for a disease in need thereof comprising, consisting essentially of, or consisting of administering an effective amount of an mTOR inhibitor to the subject.

BRIEF DESCRIPTION OF THE SEVERAL VIEWS OF THE DRAWING(S)

Figure 1B:
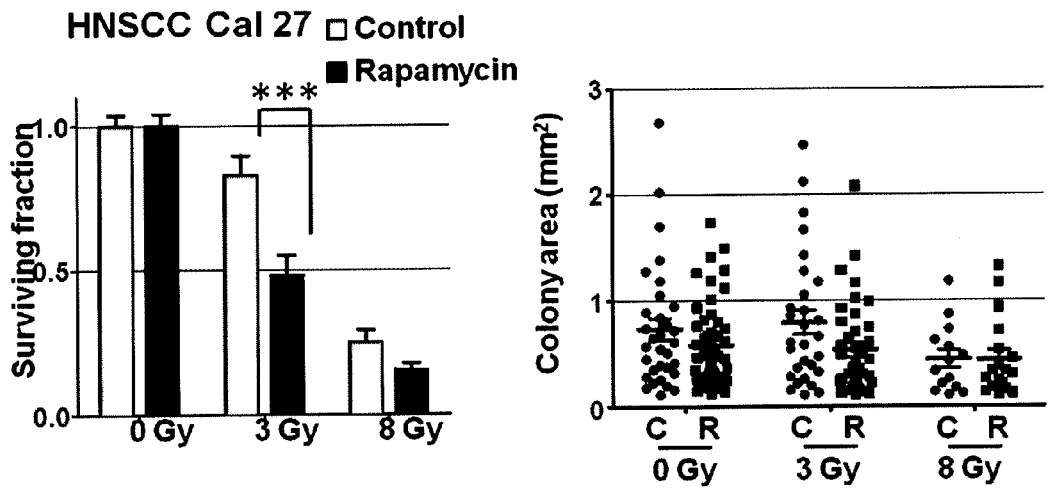
Figure 1C:
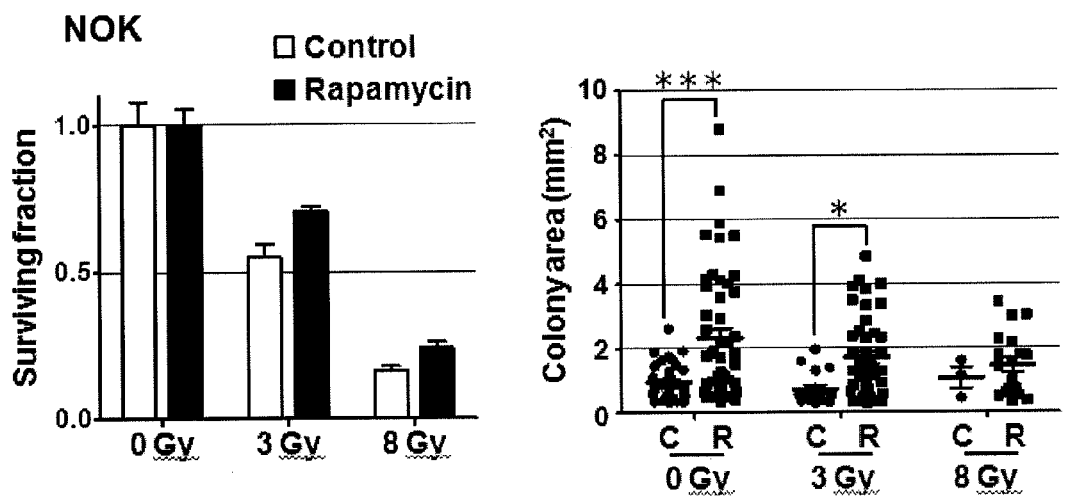
Figure 1D:
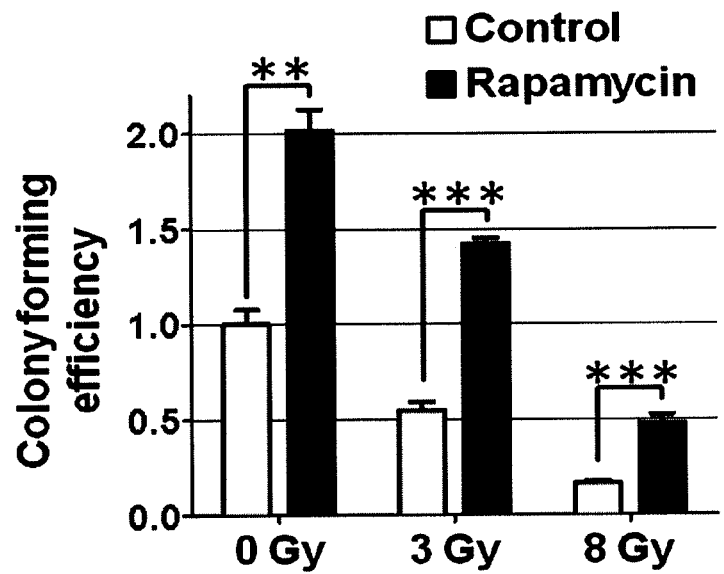

FIGS. 1A, 1B, and 1C show the surviving fractions and individual colony areas from clonogenic assays of the HNSCC cell lines HN12 (FIG. 1A) and Cal 27 (FIG. 1B) and human primary normal oral keratinocytes (NOK) (FIG. 1C) (C=control, R=rapamycin). FIG. 1D shows the colony forming efficiency from clonogenic assays of human primary NOK.

Figure 2A:
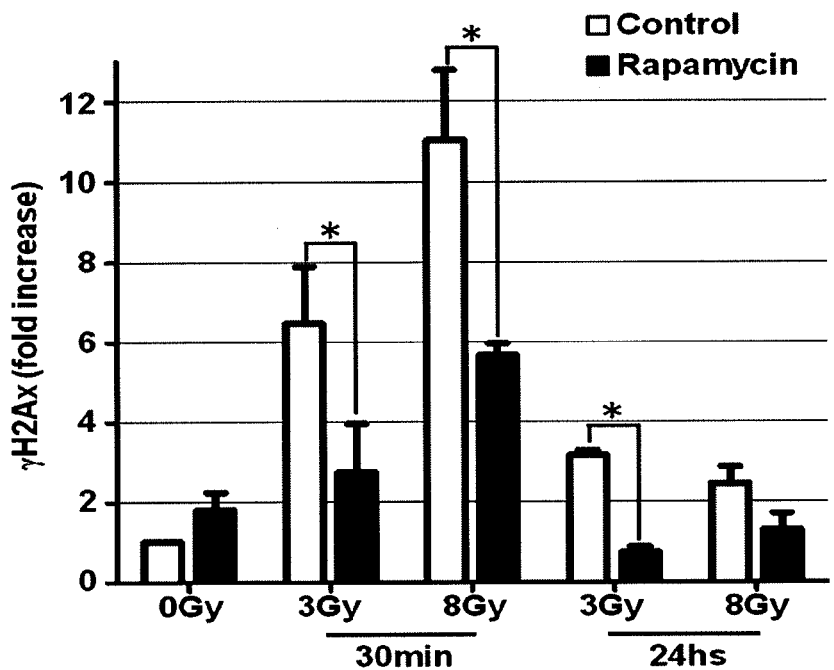
Figure 2B:
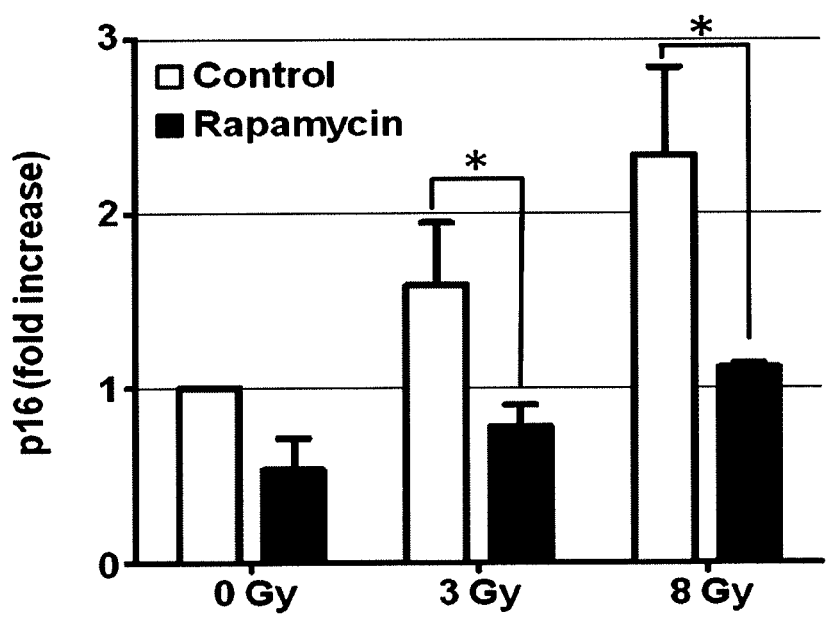
Figure 2C:
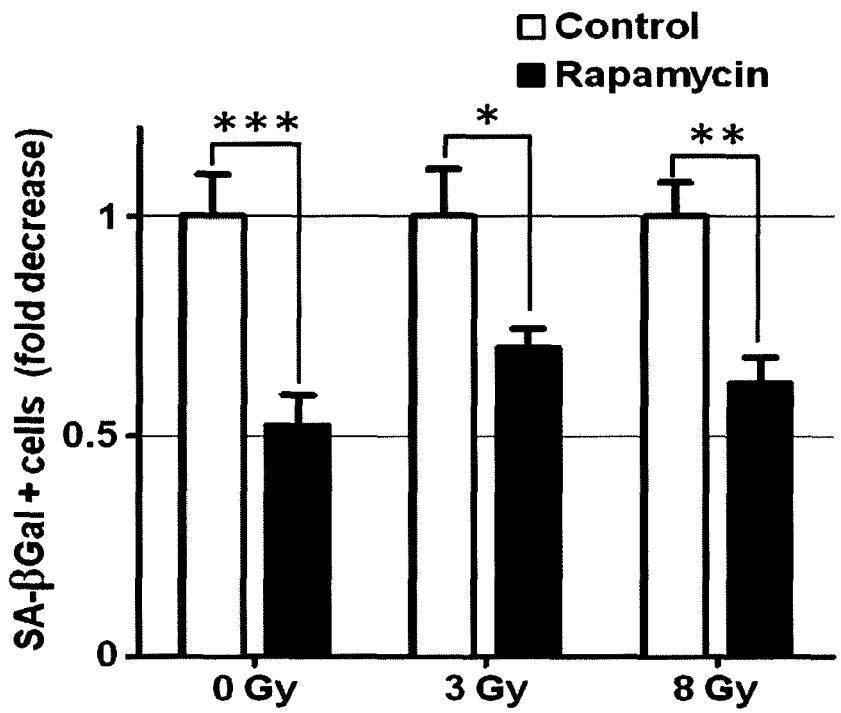

FIG. 2A shows γH2AX levels in irradiated control or rapamycin treated human primary NOK at 30 min and 24 h after the indicated dose of radiation in grays (Gy). FIG. 2B shows p16 levels in irradiated control or rapamycin treated human primary NOK after the indicated dose of radiation in grays (Gy). FIG. 2C shows the senescence-associated β-galactosidase (SA-βgal) in irradiated control (Con) or rapamycin treated human primary NOK after the indicated dose of radiation in grays (Gy) 3 days after rapamycin treatment.

Figure 3A:
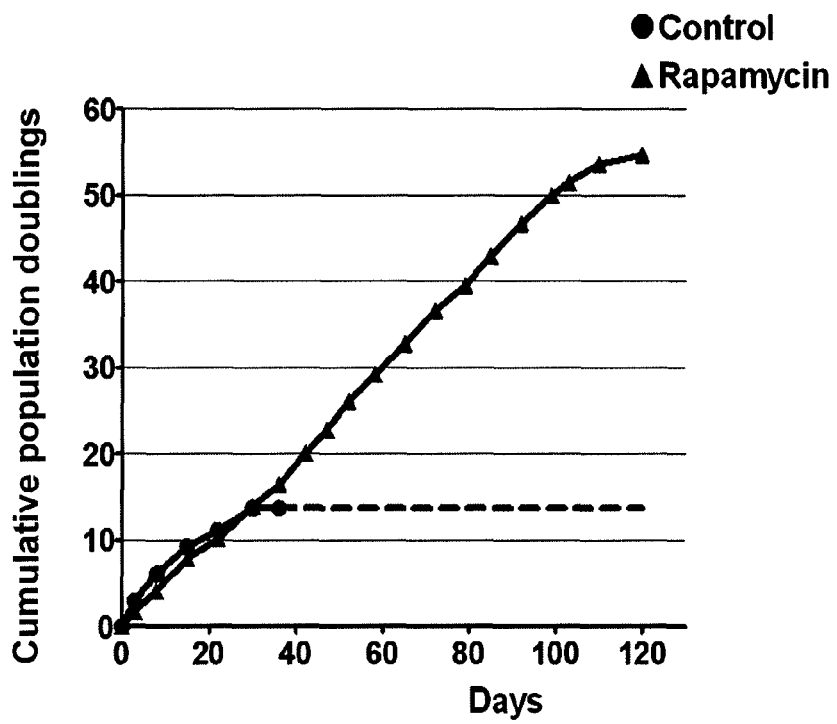
Figure 3B:
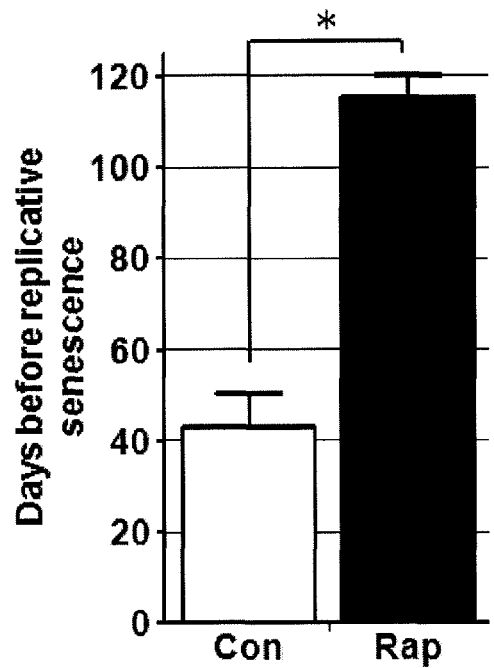
Figure 3C:
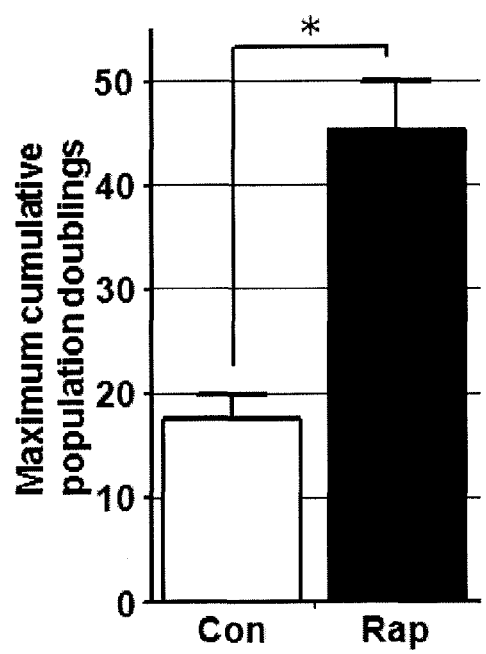

FIG. 3A shows the cumulative population doubling from a representative culture of human primary NOK in control conditions or continuous presence of rapamycin. Each dot represents a passage and dotted line indicates that cells could not be further expanded. FIGS. 3B and 3C show the average number of days before replicative senescence (FIG. 3B) and the maximum cumulative population doublings (FIG. 3C) from three different cultures of NOK cultured in control conditions (Con) or continuous presence of rapamycin (Rap).

Figure 4E:
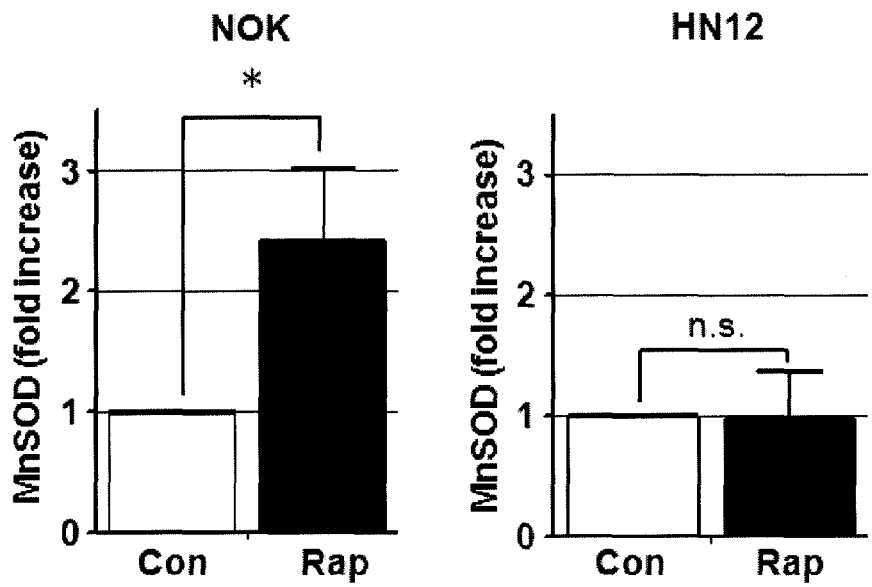
Figure 4F:
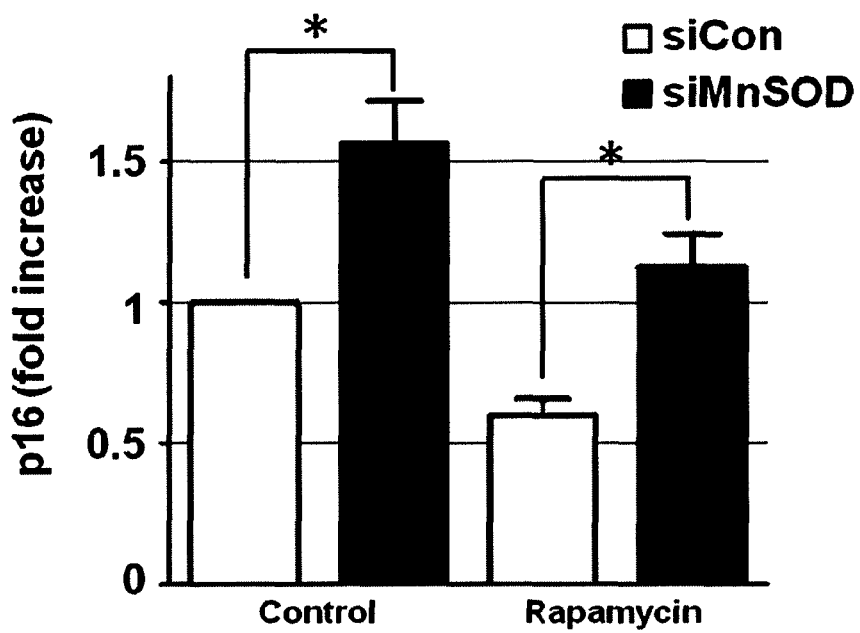
Figure 4G:
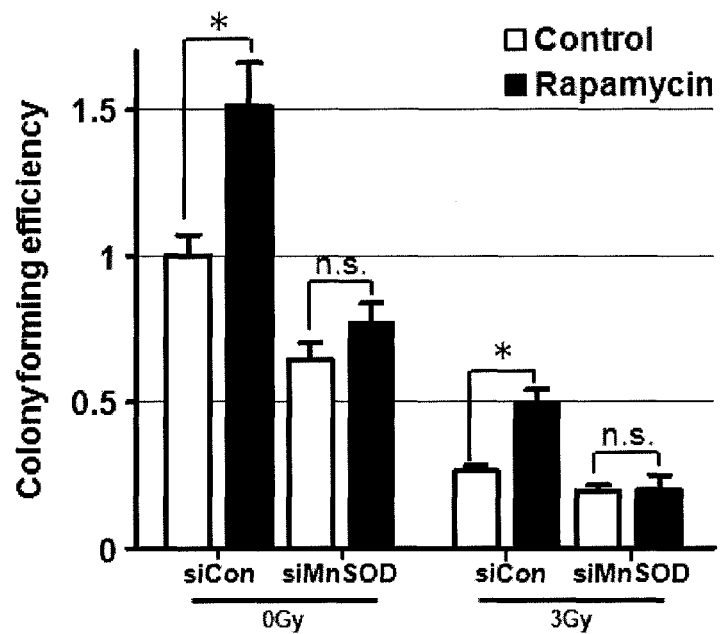

FIGS. 4A-4D show the analysis of reactive oxygen species (ROS) levels by dihydroethidium hydroethidine (DHE) staining 24 hours after radiation in NOK and HN12 cells pretreated or not (control) with rapamycin (FIGS. 4A and 4B) and fluorescent activated cell sorting (FACS) analysis of ROS levels by DHE staining in NOK after 10 or 40 days of continuous rapamycin treatment (FIGS. 4C and 4D). FIG. 4E shows the quantification of MnSOD protein expression levels by western blot in NOK and HN12 cells after 72 h of control conditions or rapamycin treatment. FIG. 4F shows p16 levels in control or rapamycin treated human primary NOK transfected with control siRNA (siCon) or siRNA targeted against MnSOD (siMnSOD). FIG. 4G shows colony forming efficiency from clonogenic assays of human primary NOK transfected with control siRNA (siCon) or siRNA targeted against MnSOD (siMnSOD). Cells were pretreated or not (control) with rapamycin for 72 h after siRNA transfection, irradiated with 0 or 3 Gy and 24 h later subjected to clonogenic assays.

Figure 5A:
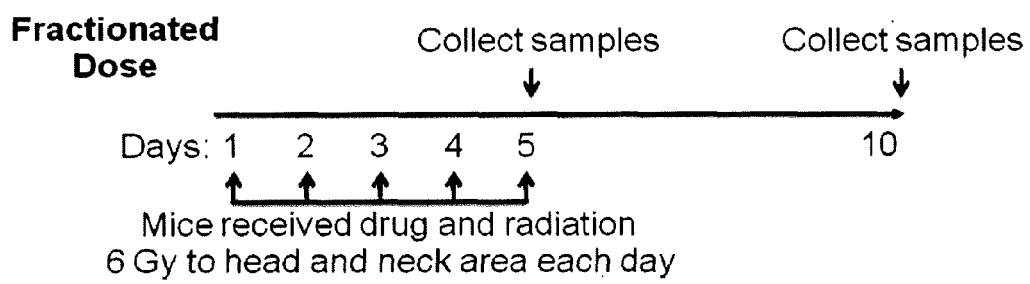
Figure 5B:
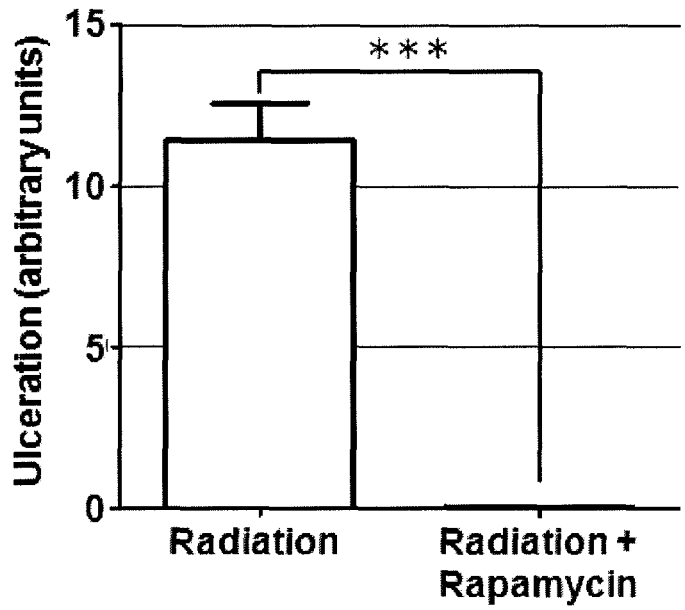

FIG. 5A shows a fractionated radiation and drug treatment scheme for mice. FIG. 5B shows quantification of ulceration in tongues stained with toluidine blue from irradiated animals on day 5 following the final radiation dose, receiving vehicle (Radiation) or rapamycin (Radiation+Rapamycin). Lack of protective epithelial barrier and therefore ulcer formation was indicated by deep, royal blue staining (not shown) in epithelium defects. Quantification represents at least 6 animals per group in 3 independent experiments.

Figure 6A:
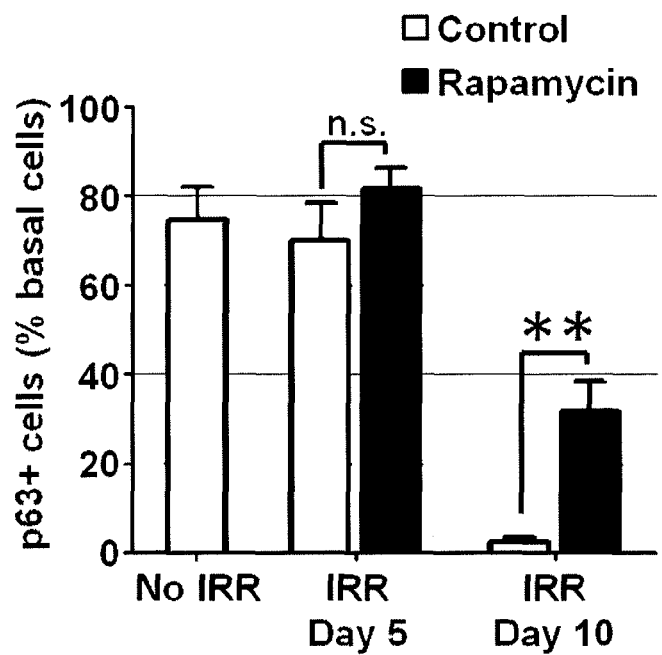
Figure 6B:
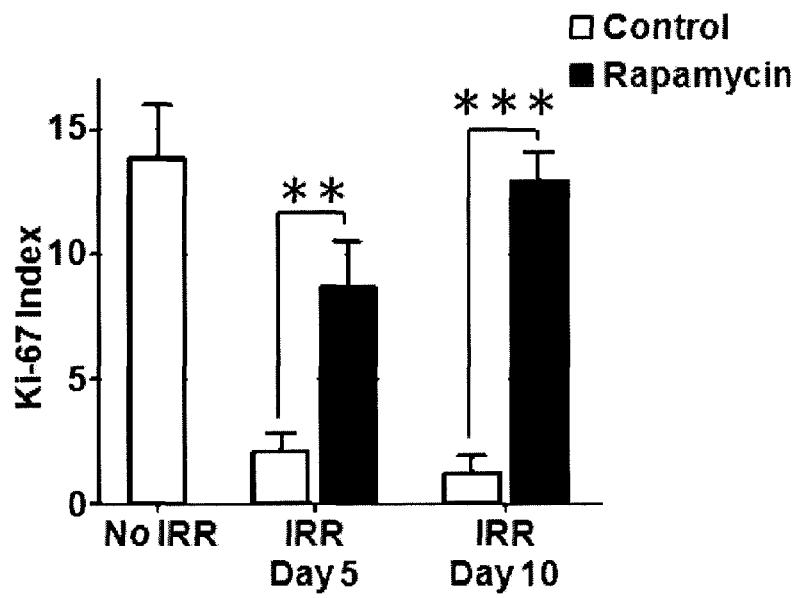
Figure 6C:
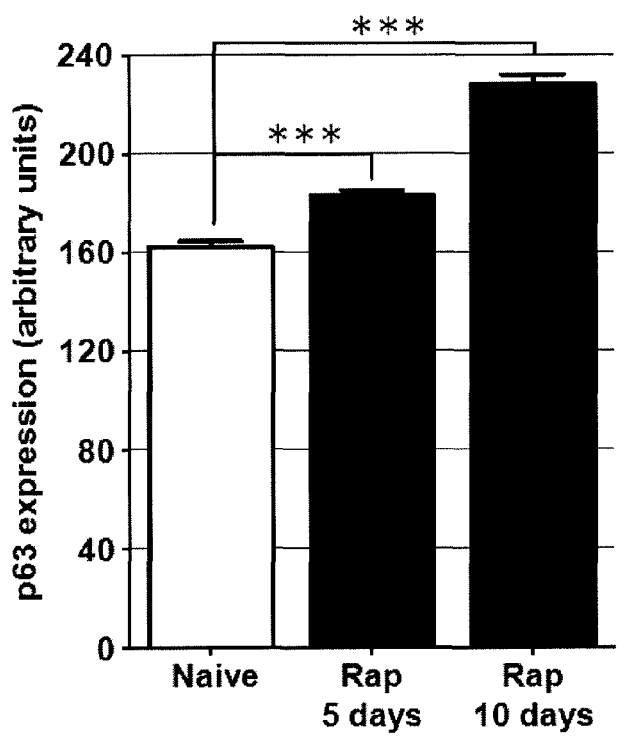

FIGS. 6A and 6B show the percentage of basal p6.3+ cells (FIG. 6A) and the Ki-67 index (percentage of Ki67+ cells/total epithelial cells) (FIG. 6B) in non-irradiated (No IRR) or irradiated (IRR) mice at day 5 and day 10 under either control conditions or rapamycin treatment. FIG. 6C shows the expression levels of the stem cell marker p63 in tongues from non-irradiated animals treated or not with rapamycin at the end of the treatment period (day 5) or 5 days after the last dose of rapamycin (day 10). FIG. 6C shows the average fluorescence value per nucleus in the basal layer, expressed in arbitrary units.

DETAILED DESCRIPTION OF THE INVENTION

The present invention provides a method of preventing the development of mucositis in a subject undergoing radiation therapy or chemotherapy for a disease in need thereof comprising, consisting essentially of, or consisting of administering an effective amount of an mTOR inhibitor to the subject. In accordance with an embodiment, rapamycin protects epithelial progenitor cells from replicative senescence, extending their life span in vitro. This protective effect of mTOR inhibition is believed to be mediated by the increased expression of mitochondrial superoxide dismutase (MnSOD), and the consequent suppression of oxidative stress caused by the accumulation of reactive oxygen species (ROS) in normal cells but not in cancer cells. In accordance with an embodiment, the present method includes inhibition of mTOR to prevent the loss of proliferative epithelial progenitor stem cells upon radiation or chemotherapy. The proposed method enhances the stem cells' tissue repopulating capacity, thereby preserving the integrity of the oral mucosa and protecting from radiation-induced mucositis in a subject. Moreover, the method enables prevention of hair loss, including minimizing or reducing hair loss, in a subject undergoing radiation therapy or chemotherapy for a disease in need thereof.

The mTOR is a serine/threonine protein kinase that regulates cell growth, cell proliferation, cell motility, cell survival, protein synthesis, and transcription. mTOR integrates the input from multiple upstream pathways, including insulin, growth factors (such as IGF-1 and IGF-2), and mitogens. mTOR also functions as a sensor of cellular nutrient and energy levels and redox status. Dysregulation of mTOR pathways is a contributing factor to various human disease processes, especially various types of cancer.

Additionally, in accordance with the present invention, it has been found that inhibition of mTOR increases the repopulating capacity of human epithelial stem cells, thereby preventing epithelial stem cell senescence. Thus, the present invention provides a method of increasing the lifespan of a normal oral keratinocyte in a subject undergoing radiation therapy or chemotherapy for a disease in need thereof comprising, consisting essentially of, or consisting of administering an effective amount of an mTOR inhibitor to the subject. As a result of mTOR inhibition, e.g., epithelial progenitor cells are preserved after radiation therapy relative to their condition prior to radiation therapy. Moreover, the level of MnSOD is increased in the normal oral keratinocyte upon administration of mTOR inhibitor compared to the level of MnSOD in the absence of mTOR inhibitor. The preservation of the normal oral keratinocyte stem cells can be measured by, for example, a decrease in the disappearance of the epithelial progenitor marker p63.

In an embodiment of the methods described herein, the mTOR inhibitor decreases the release of cytokines that comprise the "aging secretome," which are inflammatory mediators.

The invention further provides a method of reducing oxidative stress in a normal epithelial cell compared to a cancerous epithelial cell (e.g., from an oral mucosa) in a subject undergoing radiation therapy or chemotherapy for cancer comprising, consisting essentially of, or consisting of administering an effective amount of an mTOR inhibitor to the subject. It has been found that mTOR inhibition protects from oxidative stress by increasing MnSOD expression. As a result of the mTOR inhibition, the amount of ROS is reduced in a normal epithelial cell compared to a cancerous epithelial cell.

In embodiments of the methods described herein, the subject undergoing radiation therapy or chemotherapy for a disease in need thereof has cancer. The type of cancer is not particularly limited, as long as chemotherapy or radiation therapy is a prescribed treatment therefor. Examples of cancer include cancers of the head and neck, eye, skin, mouth, throat, esophagus, chest, bone, lung, colon, sigmoid, rectum, stomach, prostate, breast, ovaries, kidney, liver, pancreas, brain, intestine, heart, or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-borne tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocyctic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., eds., pp. 491 762 (15th ed. 2001). In accordance with an embodiment, the cancer is an oral cancer, such as cancer of the head and/or neck (e.g., tissues of the mouth, including tongue, gums, cheek linings, and palate, salivary glands, tonsils, or other lymph nodes) and head and neck squamous cell carcinoma (HNSCC). In another embodiment, the cancer is a cancer of the tongue.

In certain embodiments, the cancer is HNSCC, which includes the squamous cell carcinomas of the oral cavity, pharynx and larynx. The HNSCC can be, for example, a cancer of the tongue. HNSCC progression involves the sequential acquisition of genetic and epigenetic alterations in genes encoding tumor suppressors and oncogenes, together with the aberrant activity of signaling networks controlling cell proliferation, differentiation, migration, survival, and death. The most frequent genetic alterations in HNSCC include loss of heterozygosity and promoter silencing of the p16 tumor suppressor gene, and inactivating mutations in the p53 tumor suppressor gene. HNSCCs often overexpress the epidermal growth factor receptor (EGFR) and some of its active variants such as the truncated mutant form EGFR variant III (EGFRvIII), which causes its constitutive activation.

Both hereditary and environmental factors are implicated in head and neck carcinogenesis and their roles are difficult to separate. Several cancer prone syndromes are associated with an increased risk of head and neck cancer, including Lynch-II, Bloom syndrome, Fanconi anemia, ataxia telangiectasia and Li-Fraumeni syndrome. But genetic susceptibility to HNSCC is more likely to be due to various degrees of DNA maintenance after exposure to tobacco carcinogens. Mutagen sensitivity tests, polymorphism in DNA repair enzymes or in carcinogens metabolizing enzymes supports the role of heredity in HNSCC. GSTM1 and GSTT1 null phenotypes are associated with an increased risk of HNSCC. Concerning XRCC1, the Arg allele (Arg194Trp) and the Gln allele (Arg399Gln) are also linked to an increased risk of oral and pharyngeal cancers.

In accordance with an embodiment, a method of preventing the development of mucositis in a subject undergoing chemotherapy or radiation therapy comprises reducing inflammation of the oral mucosa and/or halting, ameliorating, or slowing the formation of oral ulcers, for example, delaying the onset or severity of reducing the number, surface area, or size of ulcers in oral mucosa (e.g., tissues of the soft palate, tongue, and/or cheeks). Further, in accordance with an embodiment of the invention, the preventing also includes preserving (i.e., not damaging) epithelial progenitor cells (including hair follicles and oral epithelial cells) after the subject's exposure to radiation therapy or chemotherapy relative to the cells' condition prior to the therapy. When the integrity of the epithelial progenitor cell is preserved, the formation of ulcerous lesions is prevented and/or hair loss is reduced or minimized.

The term "preventing" is meant any degree (10, 20, 30, 40, 50, 60, 70, 80, 90% or more) in inhibition of the onset of radiation- or chemotherapy-induced oral ulcers/lesions and/or mucositis, including complete inhibition of the development of radiation- or chemotherapy-induced oral ulcers/lesions and/or mucositis. Alternatively, or in addition, the onset of the development of radiation- or chemotherapy-induced oral ulcers/lesions and/or mucositis can be delayed with the methods described herein by at least one week (e.g., at least 2 weeks, at least 3 weeks, at least 1 month, at least 2 months, at least 3 months, at least 4 months).

In accordance with the invention, any suitable mTOR inhibitor can be administered, for example, the mTOR inhibitor is selected from rapamycin, prodrugs of rapamycin, 40-O-(2-hydroxyethyl)-rapamycin, 32-deoxorapamycin, 16-pent-2-ynyloxy-32-deoxorapamycin, 16-pent-2-ynyloxy-32 (S or R)-dihydro-rapamycin, 16-pent-2-ynyloxy-32 (S or R)-dihydro-40-O-(2-hydroxyethyl)-rapamycin, 40-[3-hydroxy-2-(hydroxy-methyl)-2-methylpropanoate]-rapamycin (CCI779), 40-epi-(tetrazolyl)-rapamycin (ABT578), 42-O-(2-hydroxy)ethyl rapamycin (RAD001), AP23573, TAFA-93, and biolimus, particularly, selected from rapamycin, AP23573, CCI779, RAD001, and TAFA-93. Preferably, the mTOR inhibitor is rapamycin.

Rapamycin, also known as sirolimus, is a relatively new immunosuppressant drug used to prevent rejection in organ transplantation, and is especially useful in kidney transplants. Sirolimus is a macrolide first discovered as a product of the bacterium *Streptomyces hygroscopicus* in a soil sample from an island called Rapa Nui, better known as Easter Island. Rapamycin inhibits mTOR through association with its intracellular receptor FKBP12. The FKBP12-rapamycin complex binds directly to the FKBP12-Rapamycin Binding (FRB) domain of mTOR.

The term "prodrug" denotes a derivative of a compound, which derivative, when administered to warm-blooded animals, e.g. humans, is converted into the compound (drug). The enzymatic and/or chemical hydrolytic cleavage of the compounds of the present invention occurs in such a manner that the proven drug form (parent carboxylic acid drug) is released, and the moiety or moieties split off remain nontoxic or are metabolized so that nontoxic metabolic products are produced. Non-limiting examples include esters, amides, ethers, and carbonates. Examples of prodrugs of rapamycin include such as those disclosed in United States Patent Application Publication No. 2008/0171763 A1, for example, paragraphs [0029] to [0035], [0037], and [0038], which are incorporated by reference.

In accordance with any of the embodiments, one or more than one, e.g., two, three, or more mTOR inhibitors can be administered.

In accordance with an embodiment, the methods described herein comprise administering an mTOR inhibitor in the form of a pharmaceutical composition. In particular, a pharmaceutical composition will comprise, consist essentially of, or consist of at least one mTOR inhibitor and a pharmaceutically acceptable carrier. When the pharmaceutical composition consists essentially of at least one mTOR inhibitor and a pharmaceutically acceptable carrier, compounds that exert a biological effect (e.g., an immunosuppressant, a matrix metalloprotease (MMP) inhibitor, an anticancer drug, a nonsteroidal anti-inflammatory drug (NSAID), a β-adrenergic receptor antagonist) in a subject are excluded from the pharmaceutical composition. When the pharmaceutical composition consists of at least one mTOR inhibitor and a pharmaceutically acceptable carrier, the composition excludes any other compounds. In an embodiment, the pharmaceutical composition is free of a compound that exerts a biological effect selected from an immunosuppressant, an MMP inhibitor, an anticancer drug, an NSAID, and a β-adrenergic receptor antagonist.

The pharmaceutically acceptable excipients described herein, for example, vehicles, adjuvants, carriers or diluents, are well-known to those who are skilled in the art and are readily available to the public. It is preferred that the pharmaceutically acceptable carrier be one that is chemically inert to the active compounds and one that has no detrimental side effects or toxicity under the conditions of use.

The pharmaceutical compositions can be administered orally or parenterally. Thus the compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations.

In accordance with any of the embodiments, the mTOR inhibitor can be administered orally to a subject in need thereof. Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound, or a prodrug, salt, or solvate thereof, can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly (ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the inhibitors in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The inhibitors may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topically applied compositions are generally in the form of liquids (e.g., mouthwash), creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution, such as a mouthwash. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The inhibitors, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

The dose administered to the mammal, particularly human and other mammals, in accordance with the present invention should be sufficient to affect the desired response. One skilled in the art will recognize that dosage will depend upon a variety of factors, including the age, condition or disease state, predisposition to disease, genetic defect or defects, and body weight of the mammal. The size of the dose will also be determined by the route, timing and frequency of administration as well as the existence, nature, and extent of any adverse side-effects that might accompany the administration of a particular inhibitor and the desired effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, the preventive treatment is initiated with smaller dosages that are less than the optimum dose of the compound. Thereafter, the dosage is increased by small increments until the optimum effect under the circumstances is reached. The inventive method typically will involve the administration of about 0.01 mg to about 10 mg of one or more of the inhibitors described above per kg body weight of the individual. For example, in embodiments, the inhibitors can be administered in an amount from about 0.05 mg/kg to about 5 mg/kg, from about 0.1 mg/kg to about 3 mg/kg, from about 0.5 mg/kg to about 2.5 mg/kg, from about 1 mg/kg to about 2 mg/kg, from about 1.5 mg/kg to about 1.8 mg/kg, of subject body weight per day, one or more times a day, to obtain the desired therapeutic effect.

The subject to be treated is any patient with a disease that requires chemotherapy and/or radiation therapy and typically is a mammal. The term "subject" includes humans, sheep, horses, cattle, pigs, dogs, cats, rats, and mice. In embodiments of the invention, the subject is a human.

The following examples further illustrate the invention but, of course, should not be construed as in any way limiting its scope.

EXAMPLES

Cell Culture and siRNA Transfections

NOK isolation and culture was performed as described (Leelahavanichkul and Gutkind, 2012. "Oral and Pharyngeal Epithelial Keratinocyte Culture." In Method in Molecular Biology: Epithelial Cell Culture Protocols (Humana Press)). Briefly, small (0.1-0.3 cm) gingival biopsies obtained from healthy volunteers under an NIH-approved clinical protocol (NIH-NIDCR, protocol 06D0144) were rinsed with phosphate buffer saline (PBS) and incubated with trypsin (0.25%) solution overnight at 4° C. Next day the epithelium was peeled and scraped with forceps, finely minced with scalpels and passed through a cell strainer (100 µm). Cells were pelleted at 125 g and plated in 60-mm dish coated with 0.3 mg/ml of collagen I in 1% acetic acid (BD Biosciences, Franklin Lakes, N.J.). NOK were maintained in defined keratinocyte serum free media (KSFM) (Life Technologies Corporation, Carlsbad, Calif.) supplemented with antibiotics at 37° C. in the presence of 5% $CO_2$ and passed every 3-4 days. NOK between passages 2 to 4 were used for the experiments. HN12 and Cal27 cells were maintained in Dulbecco's modified eagle medium (DMEM) (Life Technologies, Carlsbad, Calif.) supplemented with 10% fetal bovine serum (FBS) and antibiotics, at 37° C. in the presence of 5% $CO_2$. siRNAs were purchased from Thermo-Dharmacon (Lafayette, Colo.) (siGENOME SMARTpool siRNA for MnSOD, catalog M-009784-02-0005; p16, catalog M-011007-03-0005; and non-targeting control siRNA, catalog D-001206-13) and transfected at a final concentration of 80 nM using LIPOFECTAMINE™ RNAiMAX (Life Technologies Corporation, Carlsbad, Calif.), according to the manufacturer's instructions.

Irradiation and Clonogenic Assays

Cells were plated in 3.5 cm dishes and treated with vehicle or 20 nM rapamycin (LC Laboratories, Woburn, Mass.) for 3 days, and then γ-irradiated with 0 (control), 3 or 8 grays (Gy), and kept with vehicle or rapamycin for 24 h. Afterwards, cells were trypsinized, counted with an automated cell counter (Scepter Scientific Inc., Livermore, Calif.; EMD Millipore Corporation, Billerica, Mass.) and replated in duplicate in 6 well plates at 400, 800 or 1200 cells per well. Cells were grown for further 7 to 10 days and the resulting colonies were fixed in 3.2% paraformaldehyde and stained with 0.5% of crystal violet in PBS for 30 min at room temperature. Plates were washed with running water to remove excess of labeling and scanned. Colonies were counted and measured with calibrated images in ImageJ with the analyze particles function. Surviving fraction was calculated as previously described (Franken et al., *Nat. Protoc.*, 1, 2315-2319 (2006)) relative to the respective non-irradiated cells. Colony forming efficiency was determined using the same protocol but expressed as the proportion of plated cells that formed colonies relative to the number of colonies formed by non-irradiated control cells. For siRNA experiments, cells were transfected with the corresponding siRNA 24 h before rapamycin treatment as described above.

Immunoblot Analysis

Cells were treated and irradiated as described above and harvested 30 min or 24 h after radiation. Cells were lysed at 4° C. in lysis buffer (50 mM Tris-HCl, 150 mM NaCl, 1 mM EDTA, 1% Nonidet P-40) supplemented with protease (protease inhibitor cocktail, Sigma-Aldrich, St. Louis, Mo.) and phosphatase inhibitors (1 mM $Na_3VO_4$ and 1 mM NaF). Equal amounts of total cell lysate proteins were subjected to SDS-polyacrylamide gel electrophoresis and transferred to nitrocellulose membranes. Bands were detected by using near-infrared fluorescence (ODYSSEY™ LI-COR Biosciences, Lincoln, Nebr.) with goat anti-mouse coupled to IRDYE700CW™ (LI-COR Biosciences, Lincoln, Nebr.) or goat anti-rabbit coupled to ALEXA FLUOR™ 680 (Life Technologies Corporation, Carlsbad, Calif.). The relative contribution of individual bands was calculated using the ODYSSEY™ Application Software v3 (LI-COR Biosciences, Lincoln, Nebr.). Primary antibodies used were: phospho Akt 473 and 308 (1:500, Cell Signaling Technology, Danvers, Mass.), Akt (1:500, Cell Signaling Technology, Danvers, Mass.), S6 (1:500, Cell Signaling Technology, Danvers, Mass.), phospho S6 (1:500, Cell Signaling Technology, Danvers, Mass.), 4EBP (1:500, Cell Signaling Technology, Danvers, Mass.), GAPDH (1:1000, Cell Signaling Technology, Danvers, Mass.), γH2AX (1:500, Millipore Corporation, Billerica, Mass.), p16 (1:50, Santa Cruz Biotechnology, Santa Cruz, Calif.), p63 (1:500, Santa Cruz Biotechnology, Santa Cruz, Calif.), α-tubulin (1:2000, Sigma-Aldrich Co., St. Louis, Mo.), involucrin (1:2000, Sigma-Aldrich Co., St. Louis, Mo.), human p53 (1:2000, Dako, Carpinteria, Calif.), MnSOD (1:150, Santa Cruz Biotechnology, Santa Cruz, Calif.), Cu—ZnSOD (1:150, Santa Cruz Biotechnology, Santa Cruz, Calif.), Catalase (1:150, Santa Cruz Biotechnology, Santa Cruz, Calif.).

Cytokine Measurements

Cells were plated in 3.5 cm dishes and treated with vehicle or 20 nM rapamycin for 3 days in complete KSFM. Twenty-four hours prior to cytokine measurement, media was changed to KSFM without supplements. At the end of the 24 h period media and cells were harvested. Media was filtered through 0.45 µm PVDF low protein binding filter, and cytokines were analyzed by the Cytokine Core Laboratory, University of Maryland, using the LUMINEX™ Multianalyte System. The cell lysates were used to quantify cellular proteins. Values of cytokines were corrected to the protein and expressed as percentage of the control. Media that was not conditioned was completely absent of cytokines. Each value corresponds to duplicate measurements of 3 independent samples of NOK. Concentration of cytokines for cells under control conditions were (expressed as pg. of cytokine/ml/10 µg protein±SE): CXCL1 (GROα), 67±3; IL1β, 1.0±0.2; IL6, 41±7; IL8, 11.8±0.6; VEGFA, 12±2; TNF-α, 0.54±0.04.

Example 1

This example illustrated that in vitro mTOR blockade by rapamycin only slightly increased radiation-induced cancer cell death in representative HNSCC cells lines.

Cell proliferation was evaluated using incorporation of 5-ethynyl-2'-deoxyuridine (EdU) with the CLICK-IT™ EdU Cell Proliferation Assay Kit (Life Technologies, Carlsbad, Calif.). Briefly, cells were treated with rapamycin 20 nM or vehicle for 3 days and then incubated with 10 µM EdU for 6 h before fixation, permeabilization, and EdU staining, which were carried out according to the kit's protocol. Cell nuclei were stained with Hoechst 33342 (Life Technologies Corporation, Carlsbad, Calif.). The proportion of cells incorporating EdU was determined by fluorescence microscopy and quantified using ImageJ "nucleus counter" plugin as described below. Eight different fields containing approximately 60 cells each were quantified per condition.

Using HN12 and Cal27 cells as typical examples of HNSCC cells that are highly sensitive to the antitumoral activity of rapamycin (Amornphimoltham et al., Cancer Research, 65, 9953-9961 (2005)), however, a limited synergistic effect on radiation-induced cell death in vitro was detected, as judged by the surviving fraction of cells exposed to clinically-relevant, sub-lethal doses of radiation in the presence of rapamycin (FIGS. 1A and 1B). The size of the colonies growing after radiation was also not significantly affected by rapamycin, which completely inhibited mTOR activity as assessed by the phosphorylation of S6 (FIGS. 1A and 1B). Similar results were observed in a large collection of HNSCC cells (not shown). Hence, these in vitro studies suggest that inhibition of mTOR in HNSCC cells may only sensitize slightly to radiation-induced cancer cell death.

Example 2

This example demonstrates that mTOR inhibition prevents senescence in normal epithelial cells.

NOK from gingival biopsies from healthy volunteers were isolated, and it was confirmed that these cultures lacked fibroblast contamination and include epithelial stem cells exhibiting tissue regenerative capacity, as judged by organotypic co-cultures and by their ability to regenerate stratified epithelium when grafted into nude mice. NOK were plated in collagen coated LabTek chamber slides and treated with vehicle or 20 nM rapamycin for 3 days. Cells were then γ-irradiated or not, and further treated with vehicle or rapamycin for 24 h. For TUNEL assay cells were processed for staining immediately, for SA-β-gal cells were passed and assessed 4 days after plating. Apoptosis was detected using the CLICK-IT™ TUNEL ALEXA FLUOR™ 594 Imaging Assay (Life Technologies, Carlsbad, Calif.) and SA-β-gal activity was measured using the SA-β-gal kit (Cell Signaling Technology, Danvers, Mass.) according to the manufacturer's instructions. The proportion of positive cells was determined by fluorescence or transmission microscopy and quantified using ImageJ. Eight different fields containing approximately 60 cells each were quantified per condition. For the calculation of population doublings cells were cultured as described and treated with vehicle or 20 nM rapamycin. Population doublings were calculated every passage using the formula x=[log 10(NH/N1)]/log 10(2)] (Cristofalo et al., PNAS, 95, 10614-10619 (1998)), where N1 is the inoculum cell number and NH the cell harvest number. To yield the cumulated doubling doublings, the population doublings for each passage was calculated and then added to the population doubling levels of the previous passages.

A decrease in the surviving fraction of NOK undergoing rapamycin treatment was not observed (FIG. 1C). On the contrary, rapamycin enhanced the colony size of NOK compared with vehicle treated cells, and this increase was maintained after radiation (FIG. 1C). Along with the increase in colony size, rapamycin also increased the colony forming efficiency of control and irradiated human NOK (FIG. 1D). Since each large colony is expected to grow from a single surviving self-renewing epithelial stem cell (Jensen et al., Nat. Protoc., 5, 898-911 (2010)), these findings indicate that rapamycin increases the survival and repopulating capacity of epithelial progenitors, hence protecting from radiation-induced loss of this tissue regenerative cell population.

Rapamycin-treated NOK exposed to radiation show reduced levels of the DNA damage response marker γH2AX at early and late time points (FIG. 2A). The activation of the DNA damage response is one of the main mediators of cell senescence, which results in irreversible growth arrest (Kuilman et al., Genes & Development, 24, 2463-2479 (2010); Rodier et al., J. Cell. Biol., 192, 547-556 (2011)). Accordingly, reduced levels of the senescence marker p16 in rapamycin-treated NOK after radiation were observed (FIG. 2B).

The percentage of cells positive for senescence-associated beta-galactosidase (SA-βgal) was measured, a known marker of senescent cells (Debacq-Chainiaux et al., Nat. Protoc., 4, 1798-1806 (2009)). Compared with control cells, rapamycin treatment reduced the accumulation of senescent cells in both control and radiated cells (FIG. 2C). The activation of the RB tumor suppressive pathway by the accumulation of p16 is often considered a key mechanism triggering cell senescence in several systems, including skin keratinocytes (Kuilman et al., Genes & Development, 24, 2463-2479 (2010); Luis et al., Cell Stem Cell, 9, 233-246 (2011)). Knockdown of p16 in NOK resulted in an increase in the colony forming efficiency of NOK under control conditions as well as after ionizing radiation. Together, these findings suggest that mTOR inhibition may increase the clonal proliferative capacity of epithelial progenitor stem cells by preventing the activation of specific cell senescence mechanisms.

Based on these results, it was then tested if mTOR inhibition would also protect NOK from replicative senescence, a process that involves the progressive depletion of progenitor cells due to senescence and differentiation, and often serves as an in vitro surrogate for aging (Zeng, Stem Cell Reviews and Reports, 3, 270-279 (2007)). Surprisingly, continuous treatment of human primary NOK with rapamycin dramatically extended the lifespan of the cells in culture (FIG. 3A). Specifically, rapamycin treated cells almost tripled their lifespan and total cumulative population doublings when compared to control cells (FIGS. 3B and 3C). It is estimated that while in the absence of rapamycin a single cell will give rise approximately to $10^6$ cells before undergoing senescence, in the presence of rapamycin a single cell will give rise to around $10^{17}$ cells. Similar results were observed in multiple independent NOK isolates.

Western blot analysis revealed that cells continued to respond to rapamycin along the entire treatment, as assessed by the inhibition of phosphorylation of ribosomal protein S6 by rapamycin. While significant changes in the phosphorylation status of Akt were not observed, there was a clear reduction in the levels of p16 in rapamycin-treated NOK when compared to the increasing p16 expression levels with time in control cells, concomitant with a massive increase in SA-βgal in control cells but not in rapamycin treated cells.

As replicative senescence involves the progressive depletion of progenitor cells in primary cultures, the effects of rapamycin treatment on the levels of the epithelial stem cell marker p63 were analyzed (Blanpain et al., Nat. Rev. Mol. Cell Biol., 10, 207-217 (2009)). As determined by western blot analysis, rapamycin prevented the disappearance of the epithelial progenitor marker p63, indicating that mTOR inhibition reduces the depletion of stem cells from the culture. These results highlight the possibility that mTOR inhibition may increase the proliferative capacity of human primary NOK by preventing the senescence of their repopulating stem cells.

Example 3

This example demonstrates that mTOR inhibition protects epithelial cells from oxidative stress through increased MnSOD expression in an embodiment of the invention.

ROS measurement was performed by incubating cells with dihydroethidium hydroethidine (DHE) (5 mM stock solution stabilized in DMSO, MOLECULAR PROBES™, Life Technologies, Carlsbad, Calif.) at a final concentration of 1.5 µM in culture media without supplements or FBS for 10 min at 37° C. Afterwards cells were washed with PBS, detached and analyzed by fluorescent activated cell sorting (FACS). FACS analysis was performed in a FACSCALIBUR™ flow cytometer (BD Biosciences, Franklin Lakes, N.J.). GSH and GSSG were measured in NOK and HN12 cells treated for 3 days with vehicle or 20 nM of rapamycin with the GSH/GSSG-GLO™ Assay kit (Promega Corporation, Madison, Wis.) according to the manufacturer's instructions.

Total RNA was isolated from cultures and processed as described (Martin et al., Oncogene, 27, 1844-1852 (2007)). One µg of cDNA was used as template for quantitative PCR using IQ™ SYBR™ Green Supermix (Bio-Rad Laboratories, Hercules, Calif.). Samples were analyzed using a Bio-Rad ICYCLER™ IQ™ multicolor real-time PCR detection system. Oligonucleotides used for amplification were from Quiagen (Valencia, Calif.) for human MnSOD (catalog 330001 PPH01716B) and CuZnSOD (catalog 330001 PPH00234B). For immunopurification, proteins were extracted in lysis buffer (50 mM Tris-Cl pH 7.5, 150 mM NaCl, 10% glycerol, 2 mM $MgCl_2$, and 1% NP40) supplemented with a complete protease inhibitor cocktail (Sigma-Aldrich Co., St. Louis, Mo.). Protein extracts were subjected to centrifugation at 14,000 rpm for 10 min and then immunoprecipitated with specified antibodies overnight. Immunoprecipitates were extensively washed with lysis buffer and eluted with loading buffer. Antibodies used were: Acetyl-lysine antibody Cell Signaling Technology, Danvers, Mass., and MnSOD (Santa Cruz Biotechnology, Santa Cruz, Calif.).

By analyzing the levels of ROS by DHE staining, it was found that rapamycin treatment prevented the induction of ROS after radiation in primary NOK, while it failed to protect from ROS accumulation in HNSCC cells (FIGS. 4A and 4B). Furthermore, rapamycin prevented the remarkable increase in ROS preceding NOK cell growth arrest (FIG. 4C, 10 days) as well as in cells undergoing replicative senescence (FIG. 4D, 40 days). These observations suggested that mTOR inhibition might limit the accumulation of ROS in NOK by decreasing ROS formation or by accelerating their inactivation. Regarding the latter, it was hypothesized that if the protective effects of rapamycin is mediated by an increase in the cellular ROS scavenging capacity, mTOR inhibition should also protect from hydrogen peroxide ($H_2O_2$) induced senescence. Indeed, pretreatment of primary NOK with rapamycin prevented the appearance of the DNA damage marker γH2AX and the expression of the senescence marker p16 following $H_2O_2$ treatment, while it did not prevent the increase in DNA damage in HNSCC cells. These results further supported the possibility that rapamycin may prevent normal cells from entering senescence and increase their replicative capacity by suppressing ROS accumulation, and hence oxidative stress.

The levels of different enzymes involved in the detoxification of ROS were measured. Interestingly, among these, rapamycin treatment did not affect the expression of catalase or cytosolic superoxide dismutase (Cu—ZnSOD), but specifically increased the protein levels of MnSOD, the mitochondrial-localized superoxide dismutase, in NOK but not in HN12 cells (FIG. 4E). MnSOD knockdown in NOK increased the basal levels of p16 expression and DNA damage as measured by γH2AX, and this effect could only be partially rescued by rapamycin (FIG. 4F). Furthermore, decreased expression of MnSOD abrogated the increased clonogenic capacity of rapamycin-treated NOK under normal conditions and after radiation (FIG. 4G).

Example 4

This example demonstrates that mTOR inhibition prevents the development of mucositis in vivo.

Female C3H mice, which were bred in the National Cancer Institute Animal Production Area (Frederick, Md.) and free of genetic mutations, were used for this study. The mice were 7-9 weeks of age at the time of experimentation and weighed between 20 and 30 grams. All experiments were carried out under the aegis of a protocol approved by the National Cancer Institute Animal Care and Use Committee and were in compliance with the Guide for the Care and Use of Laboratory Animal (1996), National Research Council. The study was conducted in a blinded fashion. The head and neck area was irradiated by placing each animal in a specially built LUCITE™ jig in such a way that the animal could be immobilized without the use of anesthetics (Vitolo et al., Clin. Cancer Res., 10, 1807-1812 (2004)). Additionally, the jig was fitted with a LUCITE™ cone that surrounded the head and prevented head movement during radiation exposure. For single-dose radiation, mice were once injected intraperitoneally with rapamycin and irradiated at 15 Gy. For fractionated radiation, mice were injected intraperitoneally every day for 5 days with rapamycin (5 mg/kg) and irradiated at 6 Gy/day (see treatment scheme in FIG. 5A). Ionizing radiation was delivered with a THERAPAX™ DXT300 X-ray irradiator (Precision X-ray, North Branford, Conn.) by using 2.0 mm Al filtration (300 kVp) at a dose rate of 1.9 Gy/minute. After radiation, animals were removed from the jig, housed (4 or 5 animals per cage) in a climate- and light-controlled environment, and allowed free access to food and water. Mice were euthanized at day 5, one hour after the last dose of radiation, and at day 10, 5 days after the last radiation dose.

Some tongues were stained in a solution of 1% toluidine blue in 10% acetic acid and analyzed macroscopically. Repeated wiping with gauze soaked in acetic acid was continued until there was no further recovery of dye. A negative result is indicated by no dye uptake or light, diffusely stippled uptake of dye. A positive result, identified as lack of epithelium and therefore an ulcer, is indicated by deep, royal blue staining in epithelium defects. Image quantifications were performed with NIH ImageJ software; tongues were selected, an automatic threshold was applied and blue staining was quantified as the average staining intensity value per tongue (expressed in arbitrary units). Result corresponds to 6 animals and is representative of 3 independent experiments. Finally, tongues were processed and embedded in paraffin, 3-µm sections were stained with H&E and microscopic analysis was conducted. Stained slides were scanned at 40× using an Aperio SCANSCOPE™ CS (Aperio, Vista, Calif.). For immunofluorescence staining, tongues were embedded in optimal cutting temperature (OCT) compound and kept at −80° C. for cryosection.

NOK were seeded on the coverslips coated with collagen, treated and irradiated as described above. One hour after radiation cells were washed with ice-cold PBS and fixed with 3.2% paraformaldehyde in PBS. After washing three times with PBS, cells were permeabilized with TritonX100 0.1% in glycine 200 mM in PBS and nonspecific binding was blocked with 3% of bovine serum albumin (BSA) in PBS for 1 h. Fixed cells were incubated with the primary antibody (anti γH2AX; 1:800) overnight at 4° C., followed by 1.5 h incubation with the secondary antibody (goat anti-mouse ALEXA FLUOR™ 488, Life Technologies, Carlsbad, Calif.). Then nuclei were stained with Hoechst 33342 (1:2000 Life Technologies, Carlsbad, Calif.) and actin was stained with ALEXA FLUOR™ 546-phalloidin (Life Technologies, Carlsbad, Calif.) according to the manufacturers' instructions. For tissue immunostaining, cryosections were mounted in silanated slides and fixed with 3.2% paraformaldehyde in PBS. After washing three times with PBS, cells were permeabilized with TRITON™ X-100 0.5% in glycine 200 mM in PBS and non-specific binding was blocked with 3% of BSA or 10% FBS in PBS for 1 h. Slides were then incubated with the primary antibody overnight at 4° C., followed by a 1.5 h incubation with the secondary antibody (goat anti-mouse and goat anti-rabbit ALEXA FLUOR™ 488 or 546, 1:800; Life Technologies, Carlsbad, Calif.). Then nuclei were stained with Hoechst 33342 and actin was stained with ALEXA FLUOR™ 546 or 488-phalloidin (Life Technologies, Carlsbad, Calif.) according to the manufacturers' instructions. Primary antibodies used were γH2AX (1:800, Millipore Corporation, Billerica, Mass.), γH2AX-FITC (1:400, Millipore Corporation, Billerica, Mass.), pS6 (1:500, Cell Signaling), mouse p53 (1:100, Dako, Carpinteria, Calif.), mouse Ki-67 (1:100, Dako, Carpinteria, Calif.), MnSOD (1:100, Santa Cruz Biotechnology, Inc., Santa Cruz, Calif.). Images were taken using Zeiss Axio Imager Z1 microscope equipped with an Apotome device (Carl Zeiss, Maple Grove, Minn.) and a motorized stage. Tissue images were stitched from 3 to 5 different images taken with a Zeiss Plan-Apochromat 20x/0.8na objective using AxioVision 4.8 software with MosaiX (Carl Zeiss, Maple Grove, Minn.). For p63, Z scan was performed and final images are maximum intensity projections (MIP) from 4 to 5 focal planes. Final images were stitched and bright contrast adjusted with AxioVision 4.8 (Carl Zeiss, Maple Grove, Minn.).

Five days of radiation (day 5) did not result in an increase in mTOR activity in vehicle-treated animals as judged by phosphorylation of S6. However, aberrant activation of mTOR throughout the basal layer of the tongue epithelium 5 days after the last dose of radiation (day 10) was observed, which was prevented by rapamycin treatment during the radiation period. Surprisingly, mTOR inactivation by rapamycin concomitant with radiation almost completely prevented the appearance of mucositis/ulcers in irradiated mice (FIG. 5B). Histological analysis of the tongues revealed the preservation of the epithelial layer in irradiated rapamycin-treated mice, although radiation-associated tissue changes were observed. No differences were observed in response to rapamycin in non-irradiated mice. In contrast, extensive ulceration, up to 50% of the surface of the tongue, was evident in the animals treated with vehicle, which was absent in all rapamycin treated mice.

Aligned with the in vitro results, substantial differences between control and rapamycin-treated mice in the visible accumulation of p53 in basal epithelial cells after radiation were not observed. However, a reduction in the levels of γH2AX and increased levels of MnSOD were observed, indicating that rapamycin may protect normal epithelial cells from DNA damage and oxidative stress in vivo.

As shown in FIGS. 6A and 6B, it was found that rapamycin prevented the radiation-induced disappearance of the epithelial progenitor marker p63 and the basal cell marker cytokeratin 5 (FIG. 6A). Furthermore, by using the proliferation marker Ki-67, it was found that rapamycin prevented also the radiation-induced block in proliferation of the basal progenitor layer of the oral epithelia at the end of the radiation regime, and preserved the proliferative and tissue repopulating function of the basal epithelial cells 5 days after the last radiation dose (FIG. 6B). Rapamycin treatment in non-irradiated mice did not affect the number and distribution pattern of p63 positive cells (not shown); only a slight and yet significant increase in the levels of p63 expression in basal progenitor cells upon rapamycin treatment was observed (FIG. 6C). Taken together, these observations indicate that rapamycin treatment prevents the loss of proliferative capacity of the epithelial progenitor and stem cell compartment after radiation, which in turn, protects from epithelial stem cell depletion and the consequent appearance of widespread ulcers and mucositis.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of reducing the development of radiation-induced mucositis in a subject in need thereof that is concurrently undergoing radiation therapy for cancer comprising administering via application to an oral mucosa an effective amount of mammalian target of rapamycin (mTOR) inhibitor rapamycin to the subject,
wherein the cancer is an oral cancer selected from the group consisting of cancer of the head and/or neck, head and neck squamous cell carcinoma (HNSCC), and cancer of the tongue.

2. The method of claim 1, wherein epithelial progenitor cells are preserved after radiation therapy relative to their condition prior to radiation therapy or chemotherapy.

3. The method of claim 1, wherein the subject is a human.

4. The method of claim 1, wherein the cancer is cancer of the head and/or neck.

5. The method of claim 1, wherein the cancer is head and neck squamous cell carcinoma (HNSCC).

6. The method of claim 1, wherein the cancer is cancer of the tongue.

7. A method of reducing hair loss in a subject in need thereof that is concurrently undergoing radiation therapy for cancer comprising topically administering an effective amount of mammalian target of rapamycin (mTOR) inhibitor rapamycin to the subject.

8. The method of claim 7, wherein the subject is a human.

9. A method of increasing the lifespan of a normal oral keratinocyte in a subject in need thereof that is concurrently undergoing radiation therapy for cancer comprising administering via application to an oral mucosa an effective amount of mammalian target of rapamycin (mTOR) inhibitor rapamycin to the subject,
wherein the cancer is an oral cancer selected from the group consisting of cancer of the head and/or neck, head and neck squamous cell carcinoma (HNSCC), and cancer of the tongue.

10. The method of claim 9, wherein the disappearance of the epithelial progenitor marker p63 is decreased.

11. The method of claim 9, wherein the level of mitochondrial superoxide dismutase (MnSOD) is increased in the normal oral keratinocyte upon administration of rapamycin compared to the level of MnSOD in the absence of rapamycin.

12. The method of claim 9, wherein the subject is a human.

13. The method of claim 9, wherein the cancer is cancer of the head and/or neck.

14. The method of claim 9, wherein the cancer is head and neck squamous cell carcinoma (HNSCC).

15. The method of claim 9, wherein the cancer is cancer of the tongue.

16. A method of reducing oxidative stress in a normal epithelial cell compared to a cancerous epithelial cell in a subject in need thereof that is concurrently undergoing radiation therapy for cancer comprising administering via application to an oral mucosa an effective amount of mammalian target of rapamycin (mTOR) inhibitor rapamycin to the subject,
wherein
the cancer is an oral cancer selected from the group consisting of cancer of the head and/or neck, head and neck squamous cell carcinoma (HNSCC), and cancer of the tongue, and
the normal and cancerous epithelial cells are from an oral mucosa.

17. The method of claim 16, wherein the amount of reactive oxygen species (ROS) is reduced in a normal epithelial cell compared to a cancerous epithelial cell.

18. The method of claim 16, wherein the subject is a human.

19. The method of claim 16, wherein the cancer is cancer of the head and/or neck.

20. The method of claim 16, wherein the cancer is head and neck squamous cell carcinoma (HNSCC).

21. The method of claim 16, wherein the cancer is cancer of the tongue.

* * * * *